United States Patent [19]

Goto et al.

[11] Patent Number: 5,032,313
[45] Date of Patent: Jul. 16, 1991

[54] TRIFLUOROBENZENE DERIVATIVE AND LIQUID CRYSTAL COMPOSITION CONTAINING THE SAME

[75] Inventors: Yasuyuki Goto; Kisei Kitano, both of Chiba, Japan

[73] Assignee: Chisso Corporation, Ohsaka, Japan

[21] Appl. No.: 490,706

[22] Filed: Mar. 7, 1990

[30] Foreign Application Priority Data

Mar. 7, 1989 [JP] Japan .................................. 1-54150

[51] Int. Cl.$^5$ ...................... C09K 19/30; C07C 19/08
[52] U.S. Cl. ........................... 252/299.63; 252/299.01; 252/299.66; 570/129
[58] Field of Search ........... 252/299.6, 299.63, 299.66; 570/123, 129, 131, 124

[56] References Cited

U.S. PATENT DOCUMENTS

| | | | |
|---|---|---|---|
| 3,293,305 | 12/1966 | Haszeldine et al. | 570/129 X |
| 4,188,274 | 2/1980 | Fields | 204/158 HA |
| 4,545,922 | 10/1985 | Eidenschink et al. | 252/299.63 |
| 4,548,731 | 10/1985 | Sugimori et al. | 252/299.63 |
| 4,551,264 | 11/1985 | Eidenschink et al. | 252/299.63 X |
| 4,606,845 | 8/1986 | Romer et al. | 252/299.63 |
| 4,659,502 | 4/1987 | Fearon et al. | 252/299.63 X |
| 4,695,398 | 9/1987 | Goto et al. | 252/299.63 |
| 4,696,759 | 9/1987 | Isoyama et al. | 252/299.63 X |
| 4,710,315 | 12/1987 | Schad et al. | 252/299.63 |
| 4,797,228 | 1/1989 | Goto et al. | 252/299.63 |
| 4,820,443 | 4/1989 | Goto et al. | 252/299.63 |
| 4,834,905 | 5/1989 | Eidenschink et al. | 252/299.63 X |
| 4,846,998 | 7/1989 | Pohl et al. | 252/299.63 |
| 4,853,152 | 8/1989 | Goto | 252/299.63 |
| 4,883,609 | 11/1989 | Yamada | 252/299.61 |
| 4,886,621 | 12/1989 | Sage et al. | 252/299.63 X |
| 4,929,784 | 5/1990 | Klinkmann et al. | 570/129 X |
| 4,943,384 | 7/1990 | Sucrow et al. | 252/299.63 X |

FOREIGN PATENT DOCUMENTS

| | | | |
|---|---|---|---|
| 58-18326 | 2/1983 | Japan | 570/129 |
| 59-82322 | 5/1984 | Japan | 570/129 |

Primary Examiner—John S. Maples
Assistant Examiner—Richard Treanor
Attorney, Agent, or Firm—Wenderoth, Lind & Ponack

[57] ABSTRACT

A trifluorobenzene derivative having a superior stability and a large positive dielectric anisotropy value and a liquid crystal composition containing the derivative are provided, which derivative is expressed by the formula

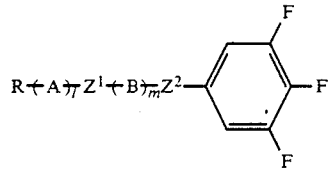

wherein R is 1-10C alkyl and one —$CH_2$— group or two not-adjacent —$CH_2$— groups in the alkyl may be replaced by O and/or —CO— and/or —COO— and/or —CH=CH—, —A— and —B— are 1,4-cyclohexylene, 1,4-phenylene, pyrimidine-2,5-diyl or 1,3-dioxane-2,5-diyl, l and m each are 0, 1 or 2 and l+m≧1, and $Z^1$ and $Z^2$ each are —COO—, —OCO—, —$CH_2CH_2$—, —$OCH_2$—, —$CH_2O$—, —CH=CH— or single bond and may be same or different.

10 Claims, No Drawings

TRIFLUOROBENZENE DERIVATIVE AND LIQUID CRYSTAL COMPOSITION CONTAINING THE SAME

BACKGROUND OF THE INVENTION

1. Field of the Invention

This invention relates to a trifluorobenzene derivative used as a component of liquid crystal materials. More particularly it relates to a trifluorobenzene derivative suitable as a component of liquid crystal compositions useful for a passive mode and an active matrix mode, each requiring a high reliability, and a liquid crystal composition containing the derivative.

2. Description of the Related Art

Liquid crystal compositions used for liquid crystal display elements of conventional passive modes such as liquid crystal compositions used for liquid crystal display elements of 90° twisted nematic mode, guest-host mode, supertwisted mode, SBE mode, etc. and further liquid crystal compositions used for liquid crystal display elements of active matrix modes such as liquid crystal compositions used for non-linear two-terminal elements of diode, etc. or three-terminal elements of thin film transistors (TFT), etc., as a switching element, are mostly liquid crystal mixtures consisting of several kinds of liquid crystal compounds and compounds similar to liquid crystals, which compounds have a CN group at the terminal group or at the side chain thereof to exhibit a positive or negative dielectric anisotropy (hereinafter abbreviated to $\Delta\epsilon$). The reason for this is that the dielectric anisotropy of the compounds, induced by the CN group, has a large positive value when the CN group is present at the terminal group, while it has a large negative value when the group is present at the side chain. For example, in the case of liquid crystal display elements of 90° twist mode occupying the most part of commercially available liquid crystal display elements, the threshold voltage in the electricity-capacity characteristic is given by the following equation containing the dielectric anisotropy value $\Delta\epsilon$ and elastic constants $K_{11}$, $K_{22}$ and $K_{33}$:

$$V_c = \pi \sqrt{\frac{k_{11} + (k_{33} - 2k_{22})/4}{\epsilon_0 \Delta\epsilon}}$$

Thus, it can be understood that when a compound having a large positive $\Delta\epsilon$ value, i.e. a compound having a CN group at its terminal group is contained in a composition, the resulting threshold voltage Vc is reduced.

On the other hand, similarly in the other modes, the threshold voltage value depends upon the $\Delta\epsilon$ value. Namely, the larger the $|\Delta\epsilon|$, the less the Vc. As to conventional liquid crystal compositions, by adjusting the content of compounds having a CN group at the terminal end or at the side chain thereof in the above-mentioned various modes, it has been possible to drive the display element at a low voltage of several volts, which is one of the largest specific features of liquid crystal display elements.

In recent years, as the use application range of liquid crystal display elements has broadened, there has been an increasing requirement liquid crystal display elements which reduce the current consumption of liquid crystal compositions, raise the specific resistivity thereof, raise the reliability thereof such as reduction in the rate of change with lapse of time and enhancing the display contrast, in the passive mode and the active matrix mode. However, a highly polarizable group such as a CN group, in spite of its contribution to the dielectric anisotropy, has raised a problem in the aspect of the above-mentioned current consumption, specific resistivity, their rate of change with lapse of time and the resulting display contrast.

While the reason has not yet been clarified by persons skilled in the art, it may be presumed that the CN group at the terminal group or at the side chain of compounds has a certain interaction with ionic impurities present in the display element, thereby having a bad influence upon the current value, specific resistivity value and the resulting display contrast. The drawbacks of compounds having such CN group, consist in, in the case of the passive mode, causing increase in the current consumption and reduction in the specific resistivity to lower the reliability in the elements, and in the aspect of display characteristics, causing display unevenness and contrast reduction, and further, in the case of the active display elements, having a larger influence upon reduction in the reliability of display elements than that in the case of the passive display elements, coupled with the influence due to the drive current of two-terminal or three-terminal elements, thereby causing increase in the current consumption and reduction in the specific resistivity. In particular, the reduction in the specific resistivity often has a further secondary bad effect of reducing the display contrast.

At present, however, most compositions containing no CN group at the terminal group or at the side chain thereof are insufficient in the aspect of the drive voltage among the various specific features of the compositions. Thus, the low voltage drive as one of the advantages of liquid crystal display elements is often not made the best use of. Recently, in order to solve such problems, a number of compounds having one or two halogen atoms, particularly one or two fluorine atoms in the aspect of viscosity, at the terminal group or at the side chain thereof have been announced.

Examples of these compounds are as follows:

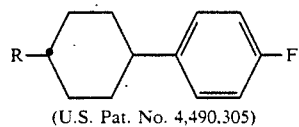

(U.S. Pat. No. 4,490,305)

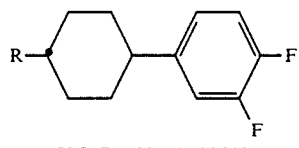

(U.S. Pat. No. 4,695,398)

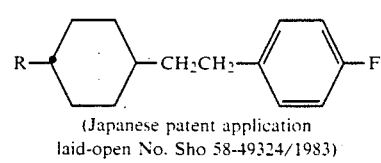

(Japanese patent application laid-open No. Sho 58-49324/1983)

-continued

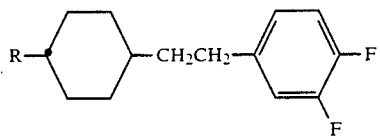
(U.S. Pat. No. 4,797,228)

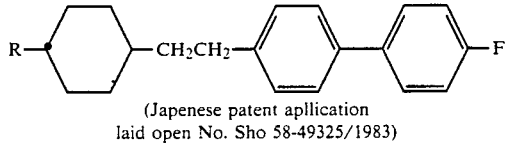
(Japenese patent apllication laid open No. Sho 58-49325/1983)

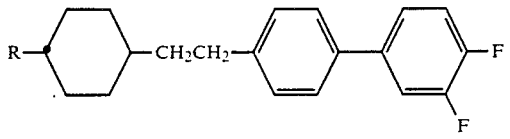
(U.S. Pat. No. 4,797,228)

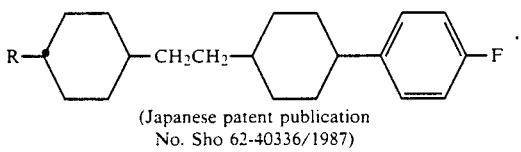
(Japanese patent publication No. Sho 62-40336/1987)

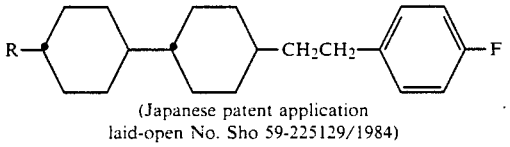
(Japanese patent application laid-open No. Sho 59-225129/1984)

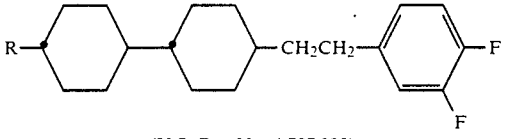
(U.S. Pat. No. 4,797,228)

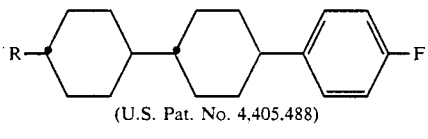
(U.S. Pat. No. 4,405,488)

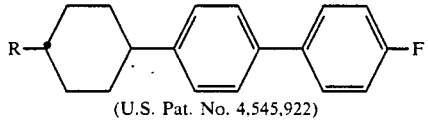
(U.S. Pat. No. 4,545,922)

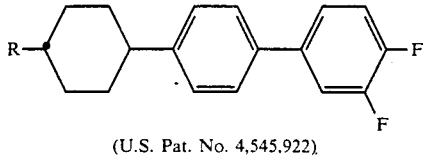
(U.S. Pat. No. 4,545,922)

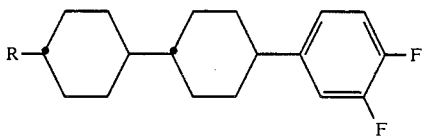
(U.S Pat. No. 4,405,488)

-continued

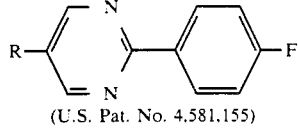
(U.S. Pat. No. 4,581,155)

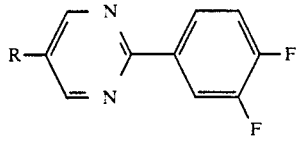
(U.S. Pat. No. 4,640,795)

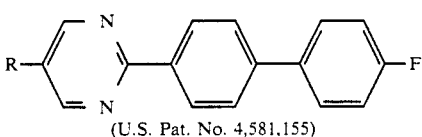
(U.S. Pat. No. 4,581,155)

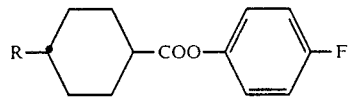

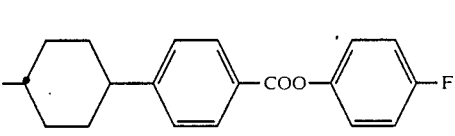
(U.S. Pat. No. 4,340,498)

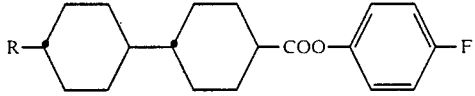

In these formulas, R represents a linear alkyl group. Most of these compounds have been reported to be liquid crystal materials having a relatively good stability and a high reliability, but they have a relatively small $\Delta\epsilon$ value of about $+3$ to $+5$, and liquid crystal compositions consisting only of these compounds have a small $\Delta\epsilon$ value to make it impossible to reduce drive voltage.

SUMMARY OF THE INVENTION

The object of the present invention is to solve these problems and provide a compound having a superior stability and a large positive $\Delta\epsilon$ value.

The present invention resides in a trifluorobenzene derivative expressed by the formula

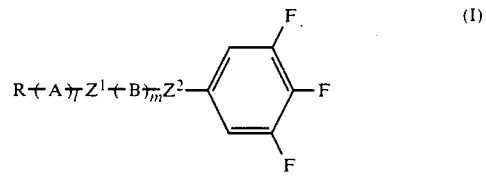

wherein R represents an alkyl group of 1 to 10 carbon atoms and one —CH$_2$— group or two not-adjacent —CH$_2$— groups present in said alkyl group may be replaced by an O atom and/or —CO—group and/or —COO—group and/or —CH=CH— group, —A— and —B— each represent 1,4-cyclohexylene, 1,4-phenylene, pyrimidine-2,5-diyl or 1,3-dioxane-2,5-diyl, l represents 0, 1 or 2, m represents 0, 1 or 2 and $l+m \geqq 1$, and $Z^1$ and $Z^2$ each represent —COO—, —OCO—, —CH$_2$CH$_2$—, —OCH$_2$—, —CH$_2$O—, —CH=CH— or a single bond and $Z^1$ and $Z^2$ may be the same or different, and a liquid crystal composition containing the above trifluorobenzene derivative.

DETAILED DESCRIPTION OF PREFERRED EMBODIMENTS

As the compound of the formula (I), compounds expressed by the following formulas Ia to Ii are mentioned:

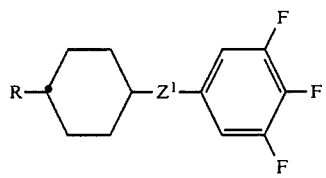
(Ia)

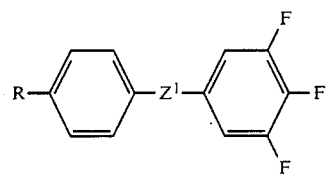
(Ib)

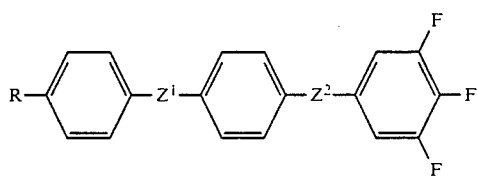
(Ic)

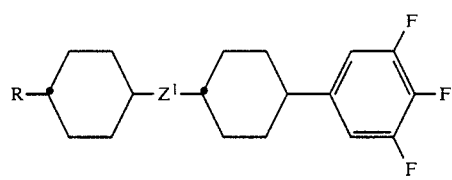
(Id)

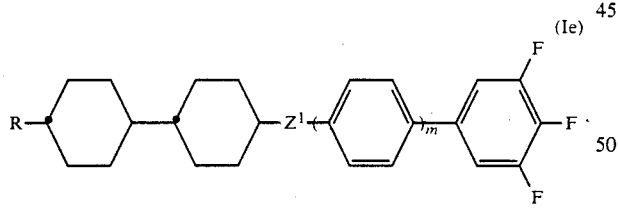
(Ie)

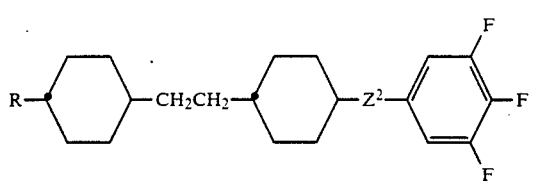
(If)

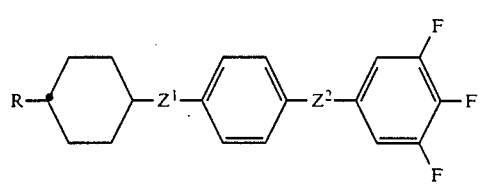
(Ig)

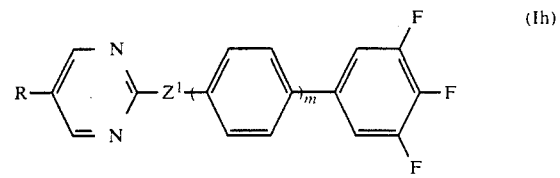
(Ih)

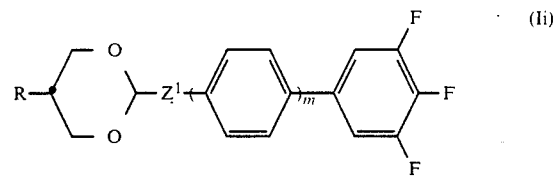
(Ii)

In these formulas, R, $Z^1$, $Z^2$ and m are as defined above.

Among the compounds of the above formulas, examples of particularly preferred compounds are expressed by the following formulas:

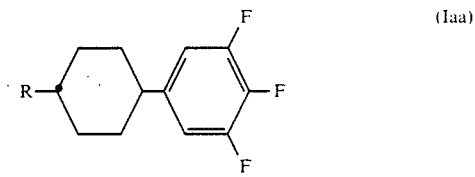
(Iaa)

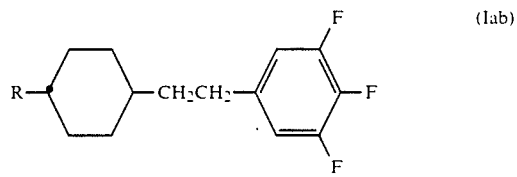
(Iab)

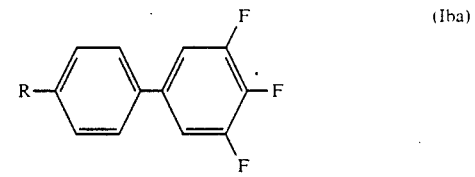
(Iba)

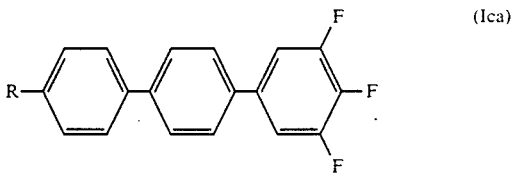
(Ica)

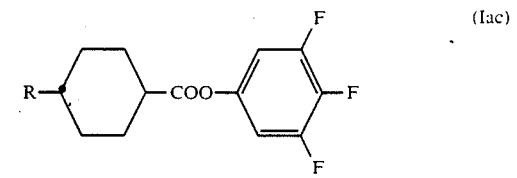
(Iac)

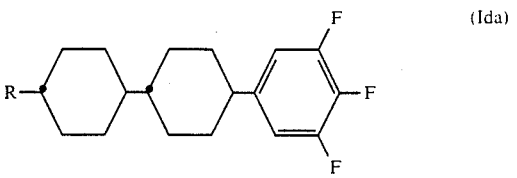
(Ida)

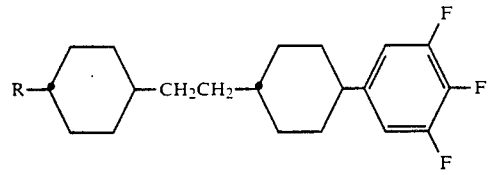 (Idb)

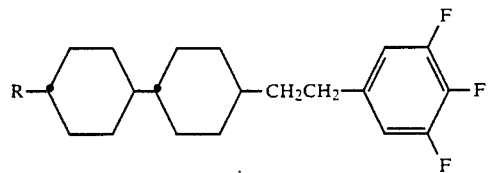 (Iea)

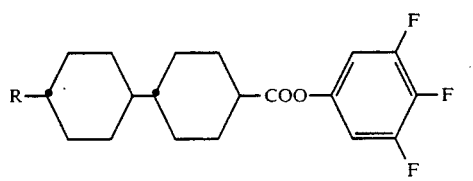 (Ieb)

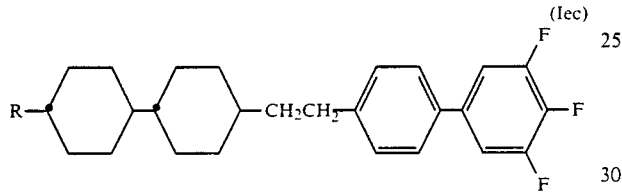 (Iec)

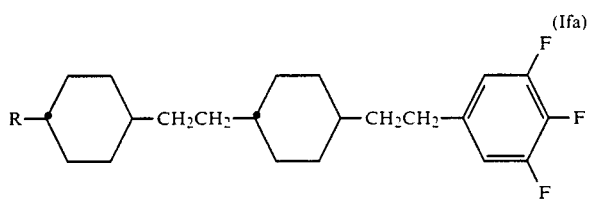 (Ifa)

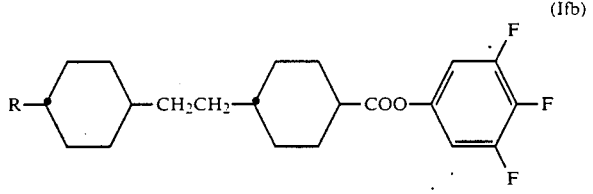 (Ifb)

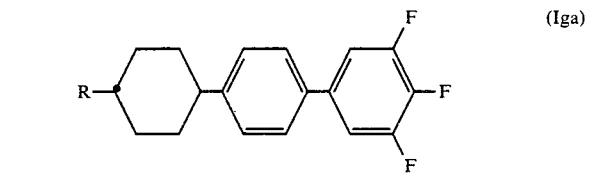 (Iga)

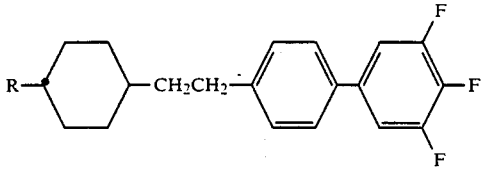 (Igb)

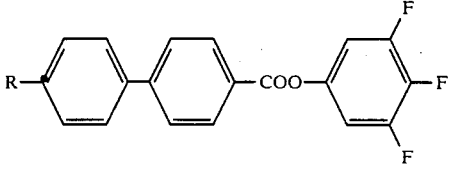 (Igc)

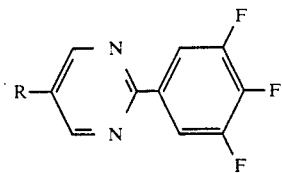 (Iha)

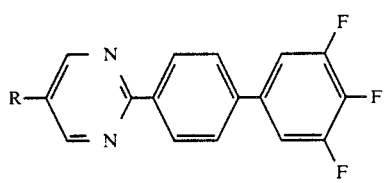 (Ihb)

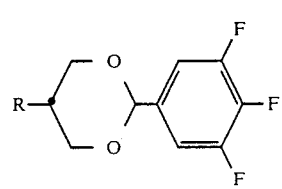 (Iia)

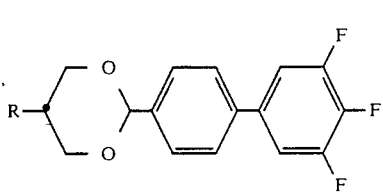 (Iib)

In these formulas, R represents an alkyl group of 1 to 10 carbon atoms and one —CH$_2$— group or two not-adjacent —CH$_2$— groups present in the alkyl group may be replaced by an O atom and/or —CO— group and/or —COO— group and/or —CH=CH— group, and R is particularly preferred to be a linear alkyl group although it may also be a branched alkyl group. The compound of the formula (I) having a branched alkyl group is more important in some cases for having an improved solubility in conventional liquid crystal bases, and particularly when such a compound is optically active, it is important as a chiral dopant. Such a kind of branched group has at most one branched chain.

The preparation of the compound of the present invention will be described. It may be carried out according to the process disclosed in the above-mentioned prior art literature.

For example, compounds expressed by the formulas Iaa, Ida and Idb may be respectively obtained by subjecting the corresponding ketone derivative and a Grignard reagent obtained from 1-bromo-3,4,5-tri-fluorobenzene to a coupling reaction to obtain an alcohol derivative, followed by subjecting this alcohol derivative to dehydration reaction in the presence of an acidic catalyst such as mineral acids e.g. sulfuric acid, hydrochloric acid, etc., Lewis acid, e.g. anhydrous aluminum chloride, ferric chloride, titanium tetrachloride, etc., organic acids, e.g. benzenesulfonic acid, p-toluenesulfonic acid, etc., to obtain a cyclohexane derivative, and successively subjecting it to a catalytic reduction in the presence of a catalyst such as developed Raney nickel, palladium/carbon, etc. to obtain a cyclohexane derivative. This preparation is illustrated by the following equations:

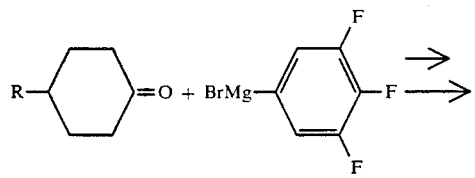

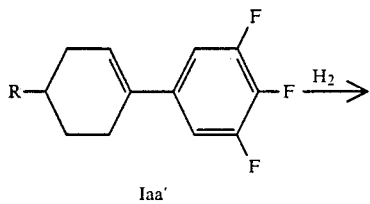

Iaa'

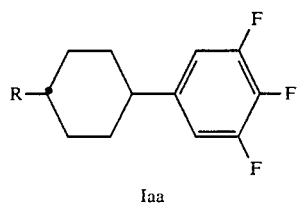

Iaa

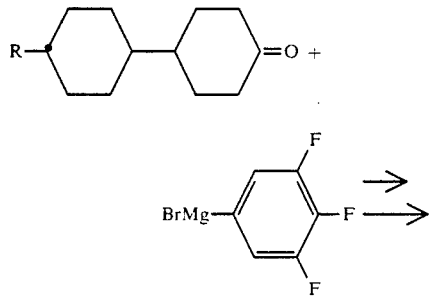

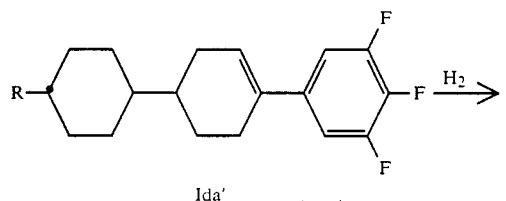

Ida'

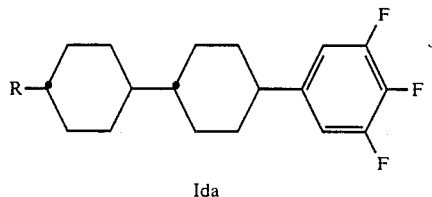

Ida

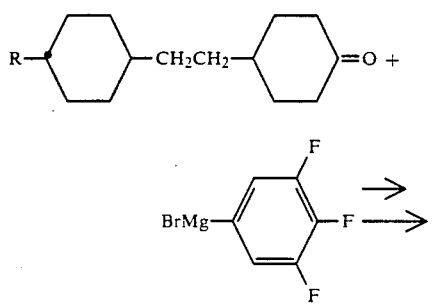

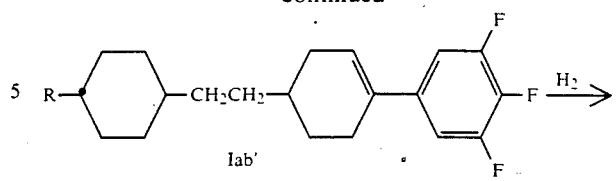

Iab'

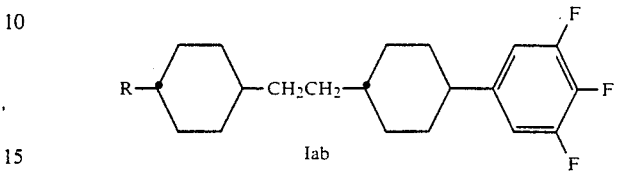

Iab

Here, when an oxidative dehydrogenation agent such as chloranil, DDQ, etc. is reacted with cyclohexene derivatives expressed by the formulas Iaa', Ida' and Idb' at the reflux temperature of an inert organic solvent such as toluene, xylene, etc., compounds expressed by the following formulas Iba, Iga and Igb can be obtained:

Iaa' ⟶ 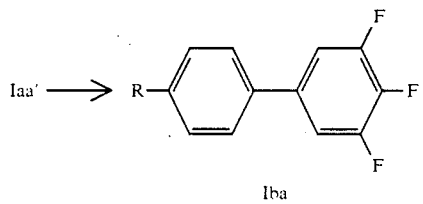

Iba

Ida' ⟶ 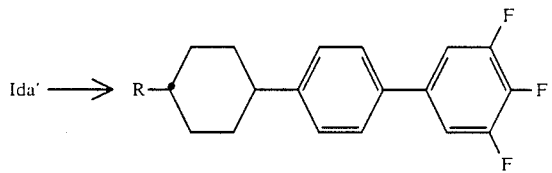

Iga

Idb' ⟶

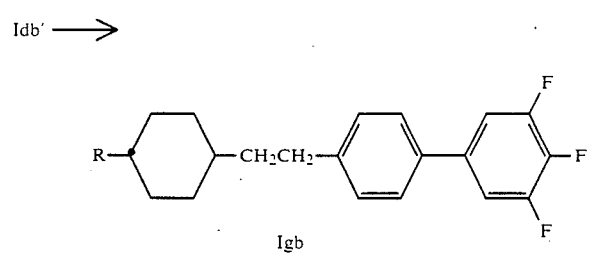

Igb

Further, the compound expressed by the formula Igb is obtained by reacting 3,4,5-trifluorobiphenyl with a substituted cyclohexyl acetyl chloride (see U.S. Pat. No. 4,797,228) in the presence of aluminium chloride to obtain a ketone derivative, followed by reducing this derivative. Further, a compound by the formula Iec can also be obtained in the same manner.

Further, compounds expressed by the formulas Iab, Iea and Ifa can be obtained by subjecting a substituted cyclohexyl acetyl chloride and a Grignard reagent prepared from 1-bromo-3,4,5-trifluorobenzene to a coupling reaction to obtain a ketone derivative and further reducing this derivative (see J. Chem, Soc., 2756 (1952)). The process is illustrated by the following reaction equations:

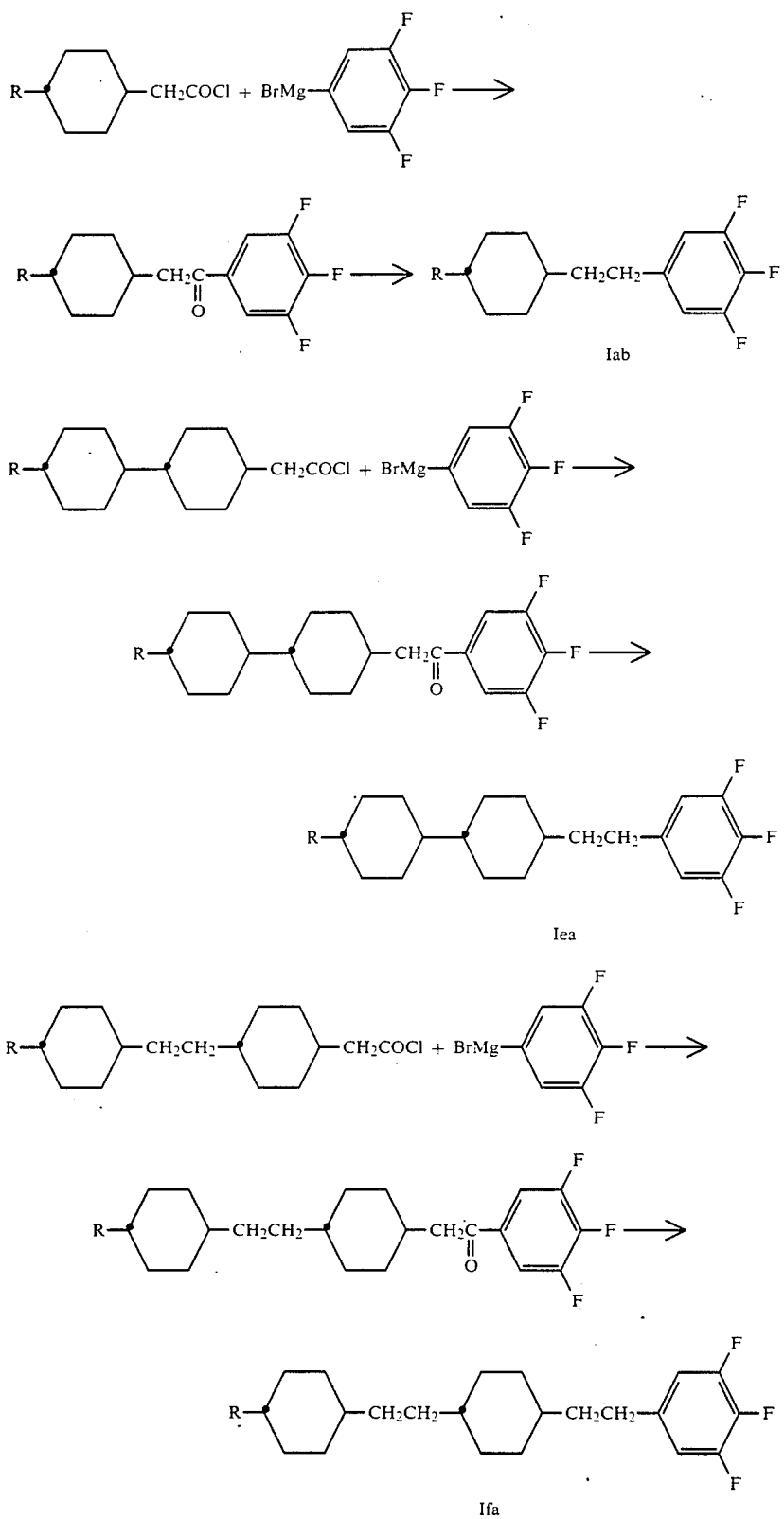

Compounds expressed by the formula Ica can be obtained by reacting a substituted cyclohexanone (see Japanese patent application laid-open No. Sho 57-167934/1982) with a Grignard reagent prepared from 1-bromo-3,4,5-trifluorobenzene, followed by the same procedure as that for obtaining compounds expressed by the formulas Iba, Iga and Igb. This process is illustrated by the following reaction equations:

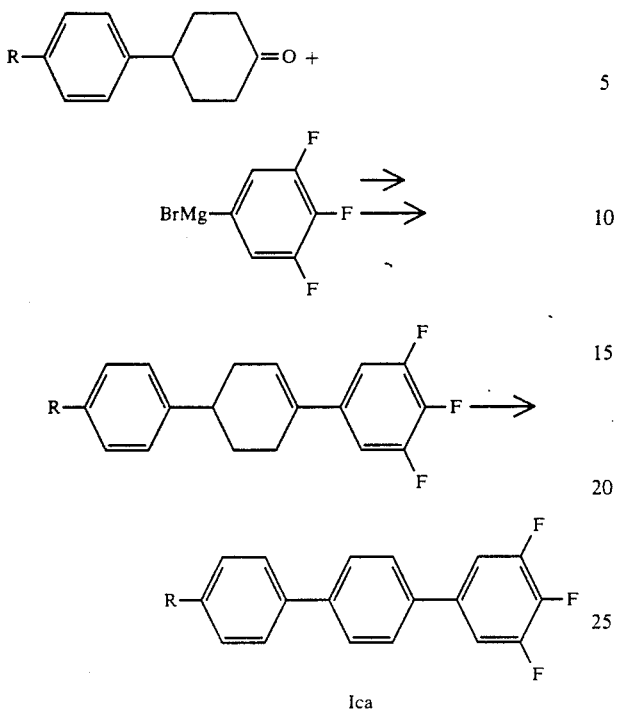

Ica

Compounds expressed by the formulas Iha and Ihb can be obtained by reacting an amidine hydrochloride, prepared from a nitrile derivative and 1-bromo-3,4,5-trifluorobenzene according to the method disclosed in Org. Synt., Col. Vol. 1, P6 (1941), with β-ethoxyacrolein in the presence of a base such as NaOH, KOH, metal alcoholates, etc. This process is illustrated by the following equation:

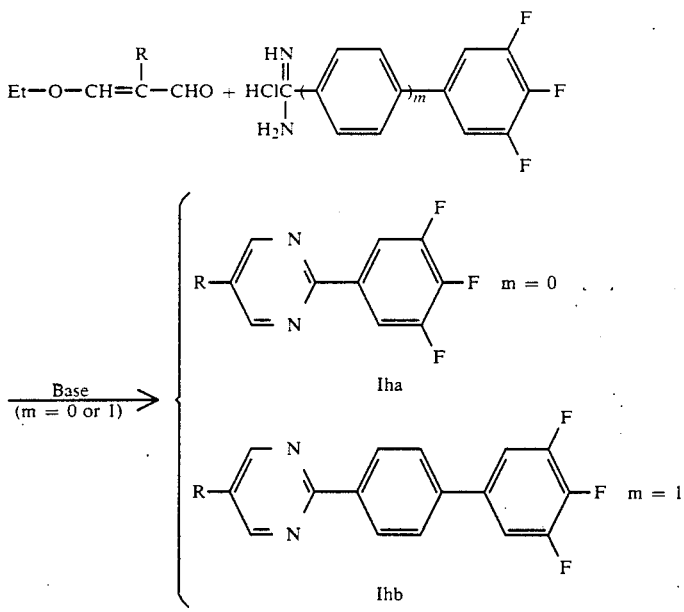

Compounds expressed by the formulas Iia and Iib can be obtained by subjecting a benzaldehyde derivative prepared by reducing a benzonitrile derivative and a substituted propanediol prepared according to a method disclosed in Japanese patent application laid-open No. Sho 55-85583/1980 to a dehydrative condensation reaction in an inert organic solvent such as benzene, toluene, methylene chloride, etc. and in the presence of an acidic catalyst such as mineral acids, Lewis acids, organic acids, etc. This process may be illustrated by the following reaction equations:

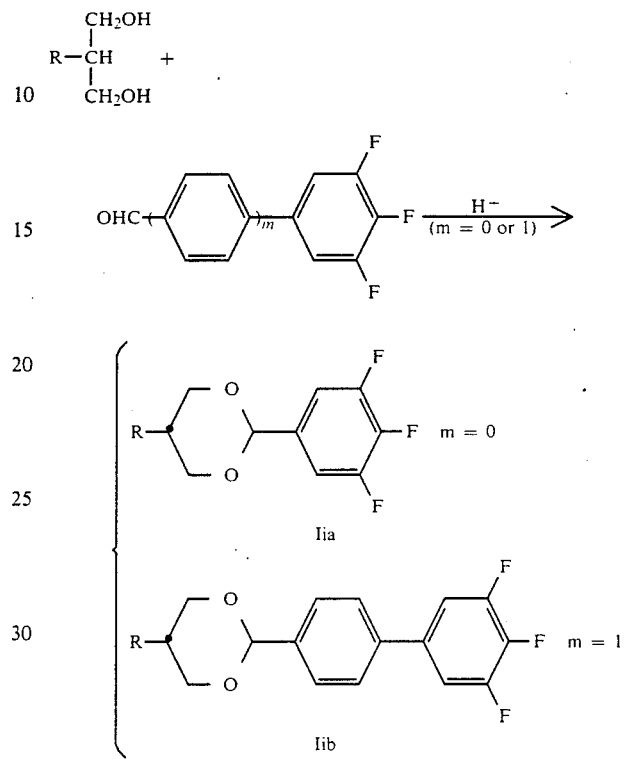

Compounds expressed by the formulas Iac, Ieb, Ifb and Igc can be obtained by reacting a carboxylic acid chloride with 3,4,5-trifluorophenol in an inert organic solvent and in the presence of a base such as pyridine, diethylamine, triethylamine, etc. This process is illustrated by the following reaction equations:

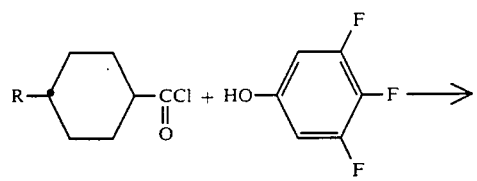

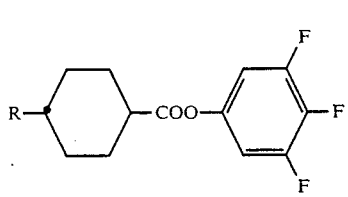

Iac

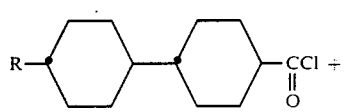

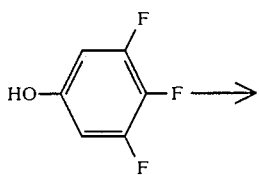

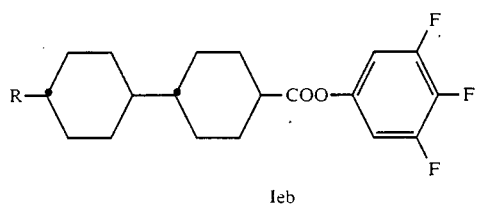

Ieb

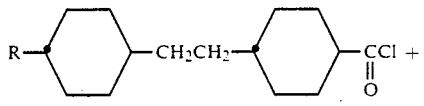

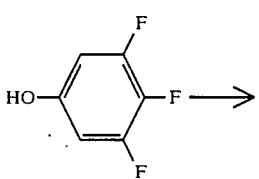

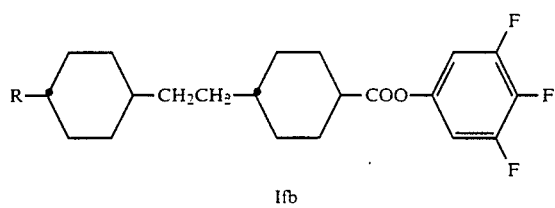

Ifb

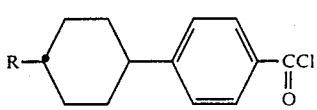

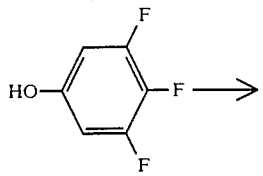

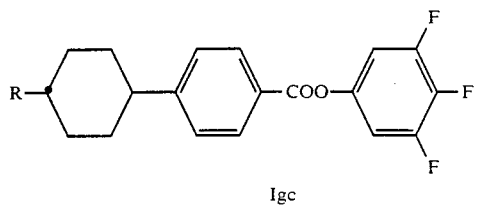

Igc

These compounds may also be prepared according to processes other than the above-mentioned ones.

The liquid crystal composition of the present invention comprises 2 to 25 components, preferably 3 to 15 components containing at least one of the compounds of the formula (I). The constituent components other than the compounds of the formula (I) are preferred to be nematic substances, particularly those selected from known substances belonging to the group consisting of azoxybenzene compounds, benzylideneaniline compounds, biphenyl compounds, terphenyl compounds, phenyl- or cyclohexyl benzoate compounds, phenyl- or cyclohexylcyclohexanecarboxylate compounds, phenylcyclohexane compounds, cyclohexylbiphenyl compounds, cyclohexylcyclohexane compounds, cyclohexylnaphthalene compounds, 1,4-biscyclohexylbenzene compounds, 4,4'-biscyclohexylbiphenyl compounds, phenylpyrimidine compounds or cyclohexylpyrimidine compounds, phenylpyridazine compounds or cyclohexylpyridazine compounds and their N-oxide compounds, phenyldioxane compounds or cyclohexyldioxane compounds, phenyl-1,3-dithian compounds or cyclohexyl-1,3-dithian compounds, 1,2-diphenylethane compounds, 1-phenyl-2-cyclohexylethane compounds, and 1,2-dicyclohexylethane compounds, and in some cases, halogenated stilbene compounds, benzyl phenyl ether compounds, tolan compounds and substituted cinnamic acid compounds.

The most important compounds suitable for the constituent components of the liquid crystal composition of the present invention can be expressed by the formula I'

$$R'—L—G—E—R'' \qquad (I')$$

wherein L and E each represent a carbocyclic or heterocyclic compound belonging to the group consisting of 1,4-disubstituted benzenes, cyclohexane ring compounds, 4,4'-disubstituted biphenyls, phenylcyclohexanes, cyclohexylcyclohexanes, 2,5-disubstituted naphthalenes, dihydronaphthalenes, tetrahydronaphthalenes, quinazolines and tetrahydroquinazolines, G represents —CH=CH—, —N(O)=N—, —CH=CY—, —CH=N(O)—, —C=C—, —CH$_2$—CH$_2$—, —CO—O—, —CH$_2$O—, —CO—S—, —CH$_2$S—, —CH=N—, —COO—Phe—COO—or a C—C single bond wherein Y represents a halogen atom, preferably chlorine atom or —CN—, and R' and R'' each represent an alkyl, an alkoxy, an alkanoyloxy or an alkoxycarbonyloxy group each of up to 18, preferably 8 carbon atoms and one of these groups may be CN, NC, NO$_2$, CF$_3$, F, Cl or Br.

In most of these compounds, R' and R" are different from each other and either one of these groups is mostly an alkyl group or an alkoxy group. However, R' and R" may be replaced by other kinds of substitutents. These substances may be obtained according to known processes. The composition of the present invention contains at least one of the compounds of the formula (I) in a quantity of about 0.1 to 40% by weight. The composition of the present invention containing at least one of the compounds of the formula (I) in a quantity of 10 to 30% by weight is particularly preferred. The composition of the present invention is produced in a manner which itself is conventional. In general, the constituting constituent components are dissolved in one another, preferably at an elevated temperature.

The present invention will be described in more detail by way of Examples, but it should not be construed to be limited thereto.

C-I point, C-N point and N-I point in these Examples mean crystal-isotropic liquid phase transition point, crystal-nematic phase transition point and nematic phase-isotropic liquid phase transition point, respectively. All of the temperatures therein indicate ° C.

Example 1

Preparation of
1-(trans-4-pentylcyclohexyl)-3,4,5-trifluorobenzene (a compound of the formula Iaa wherein R is $C_5H_{11}$—)

(Compound No. 1)

A solution of 1-bromo-3,4,5-trifluorobenzene (10.7 g, 0.051 mol) dissolved in dry tetrahydrofuran (15 ml) was reacted with magnesium (1.24 g, 0.051 mol) in nitrogen gas current at about 20° C. to prepare a Grignard reagent followed by adding to this reaction solution, a solution of 4-pentylcyclohexanone (8.6 g, 0.051 mol) dissolved in dry tetrahydrofuran (10 ml) at a rate at which the reaction temperature did not exceed 40° C. reacting the mixture while keeping the temperature at 50° C. for 2 hours, cooling the resulting material down to room temperature, adding 6N hydrochloric acid (5 ml) and water (50 ml) to the reaction solution, extracting a deposited oily substance with n-heptane (100 ml), washing the extract solution with water till it became neutral, distilling off n-heptane to obtain an oily substance of 1-(4-pentylcyclohexan-1-ol)-3,4,5-trifluorobenzene, adding potassium hydrogen sulfate (2.0 g) to the oily substance, subjecting the mixture to dehydration reaction in nitrogen gas current at 180° C. for 2 hours, cooling the resulting material down to room temperature, adding water (100 ml) and n-heptane (100 ml), separating the resulting organic layer, washing till it became neutral, distilling off n-heptane to obtain an oily substance of 1-(4-pentylcyclohexen-1-yl)-3,4,5-trifluorobenzene, dissolving this oily substance in ethyl alcohol (50 ml), adding a developed Raney nickel (1.0 g), subjecting the mixture to catalytic reduction reaction at 25° C. under the atmospheric pressure till hydrogen absorption ceased, filtering off the Raney nickel after completion of the reaction, and recrystallizing the residue from ethyl alcohol to obtain 1-(trans-4-pentylcyclohexyl)-3,4,5-trifluorobenzene (2.2 g, 7.74 mmol). C-I point: 16.7° C. Its structure was confirmed by IR and NMR.

The following compounds were obtained in the same manner as above:
Compound No.

2. 1-(Trans-4-methylcyclohexyl)-3,4,5-trifluorobenzene
3. 1-(Trans-4-ethylcyclohexyl)-3,4,5-trifluorobenzene
4. 1-(Trans-4-propylcyclohexyl)-3,4,5-trifluorobenzene
5. 1-(Trans-4-butylcyclohexyl)-3,4,5-trifluorobenzene
6. 1-(Trans-4-hexylcyclohexyl)-3,4,5-trifluorobenzene
7. 1-(Trans-4-heptylcyclohexyl)-3,4,5-trifluorobenzene
8. 1-(Trans-4-octylcyclohexyl)-3,4,5-trifluorobenzene
9. 1-(Trans-4-nonylcyclohexyl)-3,4,5-trifluorobenzene
10. 1-(Trans-4-decylcyclohexyl)-3,4,5-trifluorobenzene

EXAMPLE 2

Preparation of
1-(trans-4-butylcyclohexyl)-2-(3,4,5-trifluorophenyl)ethane (a compound of the formula Iab wherein R is $C_4H_9$—)

(Compound No. 11)

Trans-4-butylcyclohexylacetyl chloride (25 g, 0.115 mol) was dissolved in dry tetrahydrofuran (30 ml), followed by cooling the solution down to 0° C., adding iron acetylacetonate (0.81 g), agitating the mixture, adding a solution of a Grignard reagent prepared from 1-bromo-3,4,5-trifluorobenzene (25 g, 0.115 mol) and metallic magnesium (2.8 g, 0.115 mol), in tetrahydrofuran, at a rate at which the reaction temperature did not exceed 10° C., reacting the mixture at 5° C. or lower for 2 hours, adding 6N hydrochloric acid (10 ml) and water (100 ml) to the reaction solution, extracting a deposited oily substance with n-heptane (100 m(), washing the extract solution with a dilute alkali aqueous solution, washing with water till the washing water became neutral, drying over anhydrous sodium sulfate, distilling off n-heptane from the n-heptane solution, and recrystallizing the residue from ethyl alcohol to obtain 1-(trans-4butylcyclohexylacetyl)-3,4,5-trifluorobenzene (21.0 g). C-I point: 42.8° C. This compound was dissolved in ethyl acetate (100 ml), followed by adding 5% Pd supported on barium sulfate (0.5 g), subjecting the mixture to a catalytic reduction at 25° C. under 3 atm till hydrogen absorption ceased, filtering off the catalyst after completion of the reaction, and subjecting the reaction solution to a suitable purification treatment to obtain 1-(trans-4-butylcyclohexyl)-2-(3,4,5-trifluorophenyl)ethane (18.0 g). C-I point: 8.4° C.

The following compounds were obtained in the same manner as above:
Compound No.
12.   1-(trans-4-methylcyclohexyl)-2-(3,4,5-trifluorophenyl)ethane
13.   1-(trans-4-ethylcyclohexyl)-2-(3,4,5-trifluorophenyl)ethane
14.   1-(trans-4-propylcyclohexyl)-2-(3,4,5-trifluorophenyl)ethane
15.   1-(trans-4-pentylcyclohexyl)-2-(3,4,5-trifluorophenyl)ethane
16.   1-(trans-4-hexylcyclohexyl)-2-(3,4,5-trifluorophenyl)ethane
17.   1-(trans-4-heptylcyclohexyl)-2-(3,4,5-trifluorophenyl)ethane
18.   1-(trans-4-octylcyclohexyl)-2-(3,4,5-trifluorophenyl)ethane
19.   1-(trans-4-nonylcyclohexyl)-2-(3,4,5-trifluorophenyl)ethane
20.   1-(trans-4-decylcyclohexyl)-2-(3,4,5-trifluorophenyl)ethane

EXAMPLE 3

Preparation of 4'-pentyl-3,4,5-trifluorobiphenyl (a compound of the formula Iba wherein R is $C_5H_{11}$—) (Compound No. 21)

1-(4-Pentylcyclohexen-1-yl)-3,4,5-trifluorobenzene as an intermediate obtained in Example 1 (5 g) was dissolved in xylene (50 ml), followed by adding chloranil (4.5 g), reacting the mixture under reflux for 10 hours, cooling the resulting material down to room temperature, filtering off the resulting deposited hydroquinone derivative, washing the filtrate with a dilute alkali aqueous solution, washing with water till the washing water became neutral, drying over anhydrous sodium sulfate, distilling off xylene from the organic layer, dissolving the residue in n-hexane, purifying the solution according to silica gel column chromatography, collecting fractions exhibiting a single spot according to thin layer chromatography, distilling off n-hexane and recrystallizing the residue from ethyl alcohol to obtain 4'-pentyl-3,4,5-trifluorobiphenyl (3.2 g).

The following compounds were obtained in the same manner as above.
Compound No.
22. 4'-methyl-3,4,5-trifluorobiphenyl
23. 4'-ethyl-3,4,5-trifluorobiphenyl
24. 4'-propyl-3,4,5-trifluorobiphenyl
25. 4'-butyl-3,4,5-trifluorobiphenyl
26. 4'-hexyl-3,4,5-trifluorobiphenyl
27. 4'-heptyl-3,4,5-trifluorobiphenyl
28. 4'-octyl-3,4,5-trifluorobiphenyl
29. 4'-nonyl-3,4,5-trifluorobiphenyl
30. 4'-decyl-3,4,5-trifluorobiphenyl

EXAMPLE 4

Preparation of 1-[trans-4-(trans-4-propylcyclohexyl)-cyclohexyl]-3,4,5-trifluorobenzene (a compound of the formula Ida wherein R is $C_3H_7$—) (Compound No. 31)

1-[Trans-4-(trans-4-propylcyclohexyl)cyclohexyl]-3,4,5-trifluorobenzene (2.1 g) was obtained from 4-(trans-4-propylcyclohexyl)cyclohexanone (2.2 g) and 1-bromo-3,4,5-trifluorobenzene (2.0 g) in the same manner as in Example 1.

C-N point: 64.9° C., N-I point: 93.8° C.

The following compounds were obtained in the same manner as above:
Compound No.
32. 1-[trans-4-(trans-4-methylcyclohexyl)cyclohexyl]-3,4,5-trifluorobenzene
33. 1-[trans-4-(trans-4-ethylcyclohexyl)cyclohexyl]-3,4,5-trifluorobenzene
34. 1-[trans-4-(trans-4-butylcyclohexyl)cyclohexyl]-3,4,5-trifluorobenzene
35. 1-[trans-4-(trans-4-pentylcyclohexyl)cyclohexyl]-3,4,5-trifluorobenzene
36. 1-[trans-4-(trans-4-hexylcyclohexyl)cyclohexyl]-3,4,5-trifluorobenzene
37. 1-[trans 4-(trans-4-heptylcyclohexyl)cyclohexyl]-3,4,5-trifluorobenzene
38. 1-[trans-4-(trans-4-octylcyclohexyl)cyclohexyl]-3,4,5-trifluorobenzene
39. 1-[trans-4-(trans-4-nonylcyclohexyl)cyclohexyl]-3,4,5-trifluorobenzene
40. 1-[trans-4-(trans-4-decylcyclohexyl)cyclohexyl]-3,4,5-trifluorobenzene

EXAMPLE 5

Preparation of 4'-(trans-4-propylcyclohexyl)-3,4,5-trifluorobiphenyl (a compound of the formula Iga wherein R is $C_3H_7$—) (Compound No. 41)

Using 1-[4-(trans-4-pentylcyclohexyl)cyclohexen-1-yl)-3,4,5-trifluorobenzene obtained as an intermediate in Example 4 and exhibiting liquid crystal phases (C-N point: 62.4° C., N-I point: 81.9° C.), as a starting raw material, 4'-(trans-4-propylcyclohexyl)-3,4,5-trifluorobiphenyl was obtained in the same manner as in Example 3.

C-N point: 57.6° C., N-I point: 75.4° C.

The following compounds were obtained in the same manner as above:
Compound No.
42. 4'-(trans-4-methylcyclohexyl)-3,4,5-trifluorobiphenyl
43. 4'-(trans-4-ethylcyclohexyl)-3,4,5-trifluorobiphenyl
44. 4'-(trans-4-butylcyclohexyl)-3,4,5-trifluorobiphenyl
45. 4'-(trans-4-pentylcyclohexyl)-3,4,5-trifluorobiphenyl
46. 4'-(trans-4-hexylcyclohexyl)-3,4,5-trifluorobiphenyl
47. 4'-(trans-4-heptylcyclohexyl)-3,4,5-trifluorobiphenyl
48. 4'-(trans-4-octylcyclohexyl)-3,4,5-trifluorobiphenyl
49. 4'-(trans-4-nonylcyclohexyl)-3,4,5-trifluorobiphenyl
50. 4'-(trans-4-decylcyclohexyl)-3,4,5-trifluorobiphenyl

EXAMPLE 6

Preparation of 1-(trans-4-propylcyclohexyl)-2-[trans-4-(3,4,5-trifluorophenyl)cyclohexyl]ethane (a compound of the formula Idb wherein R is $C_3H_7$—) (Compound No. 51)

Using 4-[2-(trans-4-propylcyclohexyl)ethyl]cyclohexanone and 1-bromo-3,4,5-trifluorobenzene as starting raw materials, 1-(trans-4-propylcyclohexyl)-2-[trans-4-(3,4,5-trifluorophenyl)cyclohexyl]ethane was obtained in the same manner as in Example 1.

C-N point: 49.7° C., N-I point: 83.4° C.

The following compounds were obtained in the same manner as above:
Compound No.
52. 1-(trans-4-methylcyclohexyl)-2-[trans-4-(3,4,5-trifluorophenyl)cyclohexyl]ethane
53. 1-(trans-4-ethylcyclohexyl)-2-[trans-4-(3,4,5-trifluorophenyl)cyclohexyl]ethane
54. 1-(trans-4-butylcyclohexyl)-2-[trans-4-(3,4,5-trifluorophenyl)cyclohexyl]ethane
55. 1-(trans-4-pentylcyclohexyl)-2-[trans-4-(3,4,5-trifluorophenyl)cyclohexyl]ethane
56. 1-(trans-4-hexylcyclohexyl)-2-[trans-4-(3,4,5-trifluorophenyl)cyclohexyl]ethane
57. 1-(trans-4-heptylcyclohexyl)-2-[trans-4-(3,4,5-trifluorophenyl)cyclohexyl]ethane
58. 1-(trans-4-octylcyclohexyl)-2-[trans-4-(3,4,5-trifluorophenyl)cyclohexyl]ethane
59. 1-(trans-4-nonylcyclohexyl)-2-[trans-4-(3,4,5-trifluorophenyl)cyclohexyl]ethane
60. 1-(trans-4-decylcyclohexyl)-2-[trans-4-(3,4,5-trifluorophenyl)cyclohexyl]ethane

EXAMPLE 7

Preparation of 1-(trans-4-ethylcyclohexyl)-2-(3,4,5-trifluorobiphenyl-4'-yl)ethane (a compound of the formula Igb wherein R is $C_2H_5$—)

(Compound No. 61)

Using 1-(trans-4-ethylcyclohexyl)-2-[4-(3,4,5-trifluorophenyl)cyclohexen-1-yl]ethane as an intermediate of compound No. 53, exhibiting liquid crystal phases (C-I point: 45.3° C., N-I point: 37.2° C.), as a starting raw material, 1-(trans-4-ethylcyclohexyl)-2-(3,4,5-trifluorobiphenyl-4'-yl)ethane was obtained in the same manner as in Example 3. C-I point: 43.0° C. N-I point: 37.4° C.

20 The following compounds were obtained in the same manner as above:
Compound No.
62. 1-(trans-4-methylcyclohexyl)-2-(3,4,5-trifluorobiphenyl-4'-yl)ethane
63. 1-(trans-4-propylcyclohexyl)-2-(3,4,5-trifluorobiphenyl-4'-yl)ethane
64. 1-(trans-4-butylcyclohexyl)-2-(3,4,5-trifluorobiphenyl-4'-yl)ethane
65. 1-(trans-4-pentylcyclohexyl)-2-(3,4,5-trifluorobiphenyl-4'-yl)ethane
66. 1-(trans-4-hexylcyclohexyl)-2-(3,4,5-trifluorobipheny-4'-yl)ethane
67. 1-(trans-4-heptylcyclohexyl)-2-(3,4,5-trifluorobiphenyl-4'-yl)ethane
68. 1-(trans-4-octylcyclohexyl)-2-(3,4,5-trifluorobiphenyl-4'-yl)ethane
69. 1-(trans-4-nonylcyclohexyl)-2-(3,4,5-trifluorobiphenyl-4'-yl)ethane
70. 1-(trans-4-decylcyclohexyl)-2-(3,4,5-trifluorobiphenyl-4'-yl)ethane

EXAMPLE 8

Preparation of 4'''-butyl-3,4,5-trifluoroterphenyl (a compound of the formula Ica wherein R is $C_4H_9$—)

(Compound No. 71)

Using 1-[4-(4-butylphenyl)cyclohexen-1-yl]-3,4,5-trifluorobenzene obtained by reacting 4-(4-butylphenyl)cyclohexanone with 1-bromo-3,4,5-trifluorobenzene, as a starting raw material, 4'''-butyl-3,4,5-trifluoroterphenyl was obtained in the same manner as in Example 3.

The following compounds were obtained in the same manner as above:
Compound No.
72. 4'''-methyl-3,4,5-trifluoroterphenyl
73. 4'''-ethyl-3,4,5-trifluoroterphenyl
74. 4'''-propyl-3,4,5-trifluoroterphenyl
75. 4'''-pentyl-3,4,5-trifluoroterphenyl
76. 4'''-hexyl-3,4,5-trifluoroterphenyl
77. 4'''-heptyl-3,4,5-trifluoroterphenyl
78. 4'''-octyl-3,4,5-trifluoroterphenyl
79. 4'''-nonyl-3,4,5-trifluoroterphenyl
80. 4'''-decyl-3,4,5-trifluoroterphenyl

EXAMPLE 9

Preparation of 1-(trans,trans-4-propylbicyclohexyl)-2-(3,4,5-trifluorophenyl)ethane (a compound of the formula Iea wherein R is $C_3H_7$—)

(Compound No. 81)

Trans,trans-4-propylbicyclohexylacetyl chloride was reacted with a Grignard reagent prepared from 1-bromo-3,4,5-trifluorobenzene in the same manner as in Example 2 to obtain 1-(trans,trans-4-propylcyclohexylacetyl)-3,4,5-trifluorobenzene (C-I point: 97.1° C.), followed by subjecting this compound to a reduction with 5% Pd supported on barium sulfate to obtain 1-(trans,trans-4-propylbicyclohexyl)-2-(3,4,5-trifluorophenyl)ethane.

C-N point: 41.7° C., N-I point: 98.3° C.

The following compounds were obtained in the same manner as above:
Compound No.
82. 1-(trans,trans-4-methylbicyclohexyl)-2-(3,4,5-trifluorophenyl)ethane
83. 1-(trans,trans-4-ethylbicyclohexyl)-2-(3,4,5-trifluorophenyl)-ethane
84. 1-(trans,trans-4-butylbicyclohexyl)-2-(3,4,5trifluorophenyl)ethane
85. 1-(trans,trans-4-pentylbicyclohexyl)-2-(3,4,5trifluorophenyl)ethane
86. 1-(trans,trans-4-hexylbicyclohexyl)-2-(3,4,5trifluorophenyl)ethane
87. 1-(trans,trans-4-heptylbicyclohexyl)-2-(3,4,5trifluorophenyl)ethane
88. 1-(trans,trans-4-octylbicyclohexyl)-2-(3,4,5trifluorophenyl)ethane
89. 1-(trans,trans-4-nonylbicyclohexyl)-2-(3,4,5trifluorophenyl)ethane
90. 1-(trans,trans-4-decylbicyclohexyl)-2-(3,4,5trifluorophenyl)ethane

EXAMPLE 10

Preparation of 1-[trans-4-{2-(trans-4-propylcyclohexyl)ethyl}cyclohexyl]-2-(3,4,5-trifluorophenyl)ethane (a compound of the formula Ifa wherein R is $C_3H_7$—)

(Compound No. 91)

Using trans-4-[2-(trans-4-propylcyclohexyl)ethyl]-cyclohexylacetyl chloride and a Grignard reagent prepared from 1-bromo-3,4,5-trifluorobenzene, as starting raw materials, 1-[trans-4-{2-(trans-4-propylcyclohexyl)ethyl}-cyclohexyl]-2-(3,4,5-trifluorophenyl)ethane was obtained in the same manner as in Example 2.

The following compounds were obtained in the same manner as above:
Compound No.
92. 1-[trans-4-{2-(trans-4-methylcyclohexyl)ethyl}-cyclohexyl]-2-(3,4,5-trifluorophenyl)ethane
93. 1-[trans-4-{2-(trans-4-ethylcyclohexyl)ethyl}-cyclohexyl]-2-(3,4,5-trifluorophenyl)ethane
94. 1-[trans-4-{2-(trans-4-butylcyclohexyl)ethyl}-cyclohexyl]-2-(3,4,5-trifluorophenyl)ethane
95. 1-[trans-4-{2-(trans-4-pentylcyclohexyl)ethyl}-cyclohexyl]-2-(3,4,5-trifluorophenyl)ethane
96. 1-[trans-4-{2-(trans-4-hexylcyclohexyl)ethyl}-cyclohexyl]-2-(3,4,5-trifluorophenyl)ethane
97. 1-[trans-4-{2-(trans-4-heptylcyclohexyl)ethyl}-cyclohexyl]-2-(3,4,5-trifluorophenyl)ethane 98. 1-[trans-4-{2-(trans-4-octylcyclohexyl)ethyl}-cyclohexyl]-2-(3,4,5-trifluorophenyl)ethane
99. 1-[trans-4-{2-(trans-4-nonylcyclohexyl)ethyl}-cyclohexyl]-2-(3,4,5-trifluorophenyl)ethane
100. 1-[trans-4-{2-(trans-4-decylcyclohexyl)ethyl}-cyclohexyl]-2-(3,4,5-trifluorophenyl)ethane

EXAMPLE 11

Preparation of 1-(trans,trans-4-propylbicyclohexyl)-2-(3,4,5-trifluorobiphenyl-4'-yl)ethane (a compound of the formula Iec wherein R is $C_3H_7$—)

(Compound No. 101)

3,4,5-Trifluorobiphenyl (10.4 g, 0.05 mol) was dissolved in $CS_2$ (50 ml), followed by cooling the solution down to 0° C., at a time adding anhydrous aluminum chloride (6.7 g, 0.05 mol). agitating the mixture, adding a solution of trans,trans-4-propylbicyclohexylacetyl chloride (14.3 g, 0.05 mol) dissolved in $CS_2$ (20 ml) at a rate at which the reaction temperature did not exceed 5° C., successively reacting the mixture for 3 hours, adding the reaction material into a dilute aqueous solution of hydrochloric acid, extracting the deposited massive material with toluene (100 m(), washing the extract solution with a dilute alkali aqueous solution, washing with water till the washing water became neutral, drying the resulting toluene solution over anhydrous sodium sulfate, distilling off toluene and recrystallizing the residue from benzene to obtain 4'-(trans,trans-4-propylcyclohexylacetyl)-3,4,5-trifluorobiphenyl (18.4 g), dissolving this compound in ethyl acetate (100 ml), adding 5%-Pd supported on barium sulfate, subjecting the mixture to catalytic reduction at 25° C. under 3 atm, filtering off the catalyst after completion of the reaction and subjecting the reaction solution to a suitable purification treatment to obtain 1-(trans, trans-4-propylbicyclohexyl)2-(3,4,5-trifluorobiphenyl-4'-yl)ethane (12.8 g).

The following compounds were obtained in the same manner as above:
Compound No.
102. 1-(trans,trans-4-methylbicyclohexyl)-2-(3,4,5-trifluorobiphenyl-4'-yl)ethane
103. 1-(trans,trans-4-ethylbicyclohexyl)-2-(3,4,5-trifluorobiphenyl-4'-yl)ethane
104. 1-(trans,trans-4-butylbicyclohexyl)-2-(3,4,5-trifluorobiphenyl-4'-yl)ethane
105. 1-(trans,trans-4-pentylbicyclohexyl)-2-(3,4,5-trifluorobiphenyl-4'-yl)ethane
106. 1-(trans,trans-4-hexylbicyclohexyl)-2-(3,4,5-trifluorobiphenyl-4'-yl)ethane
107. 1-(trans,trans-4-heptylbicyclohexyl)-2-(3,4,5-trifluorobiphenyl-4'-yl)ethane
108. 1-(trans,trans-4-octylbicyclohexyl)-2-(3,4,5-trifluorobiphenyl-4'-yl)ethane
109. 1-(trans,trans-4-nonylbicyclohexyl)-2-(3,4,5-trifluorobiphenyl-4'-yl)ethane
110. 1-(trans,trans-4-decylbicyclohexyl)-2-(3,4,5-trifluorobiphenyl-4'-yl)ethane

EXAMPLE 12

Preparation of 3,4,5-trifluorophenyl-trans-4-propylcyclohexylcarboxylate (a compound of the formula Iac wherein R is $C_3H_7$—)

(Compound No. 111)

3,4,5-Trifluorophenol (5.0 g, 0.034 mol), which was obtained by reacting a Grignard reagent of 1-bromo-3,4,5-trifluorobenzene with acetyl chloride, oxidizing the resulting 1-acetyl-3,4,5-trifluorobenzene with a peracid to obtain 3,4,5-trifluorophenyl acetate and subjecting this acetate to hydrolysis reaction, was dissolved in dry pyridine (10 ml), followed by gradually adding trans-4-propyl-cyclohexylcarbonyl chloride (6.4 g), allowing the resulting reaction solution to stand at 50° C. for 3 hours, adding water (100 ml) to the reaction solution, extracting the resulting deposited oily substance with n-heptane (30 ml), washing the n-heptane solution with a dilute hydrochloric acid aqueous solution and then with a dilute alkali aqueous solution, further washing with water till the washing water became neutral, drying the n-heptane solution over anhydrous sodium sulfate, distilling off n-heptane and recrystallizing the resulting oily substance from ethyl alcohol to obtain 3,4,5-trifluorophenyltrans-4-propylcyclohexyl carboxylate (6.5 g).C-I: 4.5° C.

The following compounds were obtained in the same manner as above:
Compound No.
112. 3,4,5-trifluorophenyl-trans-4-methylcyclohexylcarboxylate
113. 3,4,5-trifluorophenyl-trans-4-ethylcyclohexylcarboxylate
114. 3,4,5-trifluorophenyl-trans-4-butylcyclohexylcarboxylate
115. 3,4,5-trifluorophenyl-trans-4-pentylcyclohexylcarboxylate
116. 3,4,5-trifluorophenyl-trans-4-hexylcyclohexylcarboxylate
117. 3,4,5-trifluorophenyl-trans-4-heptylcyclohexylcarboxylate
118. 3,4,5-trifluorophenyl-trans-4-octylcyclohexylcarboxylate
119. 3,4,5-trifluorophenyl-trans-4-nonylcyclohexylcarboxylate
120. 3,4,5-,trifluorophenyl-trans-4-decylcyclohexylcarboxylate
121. 3,4,5-trifluorophenyl-trans,trans-4-methylbicyclohexylcarboxylate
122. 3,4,5-trifluorophenyl-trans,trans-4-ethylbicyclohexylcarboxylate
123. 3,4,5-trifluorophenyl-trans,trans-4-propylbicyclohexyloarboxylate (C-N: 52.1° C., N-I: 117 °C.)
124. 3,4,5-trifluorophenyl-trans,trans-4-butylbicyclohexylcarboxylate
125. 3,4,5-trifluorophenyl-trans,trans-4-pentylbicyclohexylcarboxylate
126. 3,4,5-trifluorophenyl-trans,trans-4-hexylbicyclohexylcarboxylate
127. 3,4,5-trifluorophenyl-trans,trans-4-heptylbicyclohexylcarboxylate
128. 3,4,5-trifluorophenyl-trans,trans-4-octylbicyclohexylcarboxylate
129. 3,4,5-trifluorophenyl-trans,trans-4-nonylbicyclohexylcarboxylate 130. 3,4,5-trifluorophenyl-trans,trans-4-decylbicyclohexylcarboxylate
131. 3,4,5-trifluorophenyl-trans-4-methylcyclohexylbenzoate
132. 3,4,5-trifluorophenyl-trans-4-ethylcyclohexylbenzoate
133. 3,4,5-trifluorophenyl-trans-4-propylcyclohexylbenzoate (C-I: 96.9° C., N-I: 73.7° C.).
134. 3,4,5-trifluorophenyl-trans-4-butylcyclohexylbenzoate
135. 3,4,5-trifluorophenyl-trans-4-pentylcyclohexylbenzoate
136. 3,4,5-trifluorophenyl-trans-4-hexylcyclohexylbenzoate
137. 3,4,5-trifluorophenyl-trans-4-heptylcyclohexylbenzoate
138. 3,4,5-trifluorophenyl-trans-4-octylcyclohexylbenzoate
139. 3,4,5-trifluorophenyl-trans-4-nonylcyclohexylbenzoate
140. 3,4,5-trifluorophenyl-trans-4-decylcyclohexylbenzoate
141. 3,4,5-trifluorophenyl-trans-4-[2-(trans-4-methylcyclohexyl)ethyl]cyclohexylcarboxylate
142. 3,4,5-trifluorophenyl-trans-4-[2-(trans-4-ethylcyclohexyl)ethyl]cyclohexylcarboxylate
143. 3,4,5-trifluorophenyl-trans-4-[2-(trans-4-propylcyclohexyl)ethyl]cyclohexylcarboxylate
144. 3,4,5-trifluorophenyl-trans-4-[2-(trans-4-butylcyclohexyl)ethyl]cyclohexylcarboxylate
145. 3,4,5-trifluorophenyl-trans-4-[2-(trans-4-pentylcyclohexyl)ethyl]cyclohexylcarboxylate
146. 3,4,5-trifluorophenyl-trans-4-[2-(trans-4-hexylcyclohexyl)ethyl]cyclohexylcarboxylate
147. 3,4,5-trifluorophenyl-trans-4-[2-(trans-4-heptylcyclohexyl)ethyl]cyclohexylcarboxylate
148. 3,4,5-trifluorophenyl-trans-4-[2-(trans-4-octylcyclohexyl)ethyl]cyclohexylcarboxylate
149. 3,4,5-trifluorophenyl-trans-4-[2-(trans-4-nonylcyclohexyl)ethyl]cyclohexylcarboxylate
150. 3,4,5-trifluorophenyl-trans-4-[2-(trans-4-decylcyclohexyl)ethyl]cyclohexylcarboxylate

EXAMPLE 13

Preparation of
2-(3,4,5-trifluorophenyl)-5-pentyl-1,3-dioxane (a compound of the formula IIa wherein R is $C_5H_{11}-$)
(Compound No. 151)

3,4,5-Trifluorobenzaldehyde (1.6 g, 0.01 mol), which was obtained by cyanogenating 1-bromo-3,4,5-trifluorobenzene and reducing the resulting 3,4,5-trifluorobenzonitrile with diisobutylaluminum hydride , 2-pentyl-1,3-diol (1.5 g, 0.01 mol), which was obtained according to the process disclosed in Japanese patent application laid-open No. Sho 55-85583/1980, and p-toluene sulfonic acid (10 mg) were dissolved in dry toluene (30 ml), followed by reacting the solution under reflux for one hour while removing water formed by the reaction to the outside of the system, to complete the reaction, allowing the reaction solution to cool down to room temperature, adding water to the reaction material, washing the resulting toluene solution with a dilute alkali aqueous solution and then with water till the washing water became neutral, drying the toluene solution over anhydrous sodium sulfate, distilling off toluene and subjecting the residue to a suitable purification treatment to obtain 2-(3,4,5-trifluorophenyl)-5-pentyl-1,3-dioxane (1.6 g).

The following compounds were obtained in the same manner as above:
Compound No.
152. 2-(3,4,5-trifluorophenyl)-5-methyl-1,3-dioxane
153. 2-(3,4,5-trifluorophenyl)-5-ethyl-1,3-dioxane
154. 2-(3,4,5-trifluorophenyl)-5-propyl-1,3-dioxane
155. 2-(3,4,5-trifluorophenyl)-5-butyl-1,3-dioxane
156. 2-(3,4,5-trifluorophenyl)-5-pentyl-1,3-dioxane
157. 2-(3,4,5-trifluorophenyl)-5-hexyl-1,3-dioxane
158. 2-(3,4,5-trifluorophenyl)-5-octyl-1,3-dioxane
159. 2-(3,4,5-trifluorophenyl)-5-nonyl-1,3-dioxane
160. 2-(3,4,5-trifluorophenyl)-5-decyl-1,3-dioxane
161. 2-(3,4,5-trifluorobiphenyl-4'-yl)-5-methyl-1,3-dioxane
162. 2-(3,4,5-trifluorobiphenyl-4'-yl)-5-ethyl-1,3-dioxane
163. 2-(3,4,5-trifluorobiphenyl-4'-yl)-5-propyl-1,3-dioxane
164. 2-(3,4,5-trifluorobiphenyl-4'-yl)-5-butyl-1,3-dioxane
165. 2-(3,4,5-trifluorobiphenyl-4'-yl)-5-pentyl-1,3-dioxane
166. 2-(3,4,5-trifluorobiphenyl-4'-yl)-5-hexyl-1,3-dioxane
167. 2-(3,4,5-trifluorobiphenyl-4'-yl)-5-heptyl-1,3-dioxane
168. 2-(3,4,5-trifluorobiphenyl-4'-yl)-5-octyl-1,3-dioxane
169. 2-(3,4,5-trifluorobiphenyl-4'-yl)-5-nonyl-1,3-dioxane
170. 2-(3,4,5-trifluorobiphenyl-4'-yl)-5-decyl-1,3-dioxane

EXAMPLE 14

Preparation of
2-(3,4,5-trifluorophenyl)-5-pentyl-1,3-pyrimidine (a compound of the formula Iha wherein R is $C_5H_{11}-$)
(Compound No. 171)

3,4,5-Trifluorobenzamidine hydrochloride (12.6 g) and α-pentyl-β-ethoxyacrolein (10.2 g) were added into a solution of sodium methylate prepared by dissolving sodium (2.8 g) in anhydrous methanol (20 ml), followed by reacting the mixture at the reflux temperature with stirring for 6 hours, distilling off methanol after completion of the reaction, adding toluene (20 ml) to the reaction residue, extracting the resulting material, washing the resulting toluene extract solution with water till the washing water became neutral, drying the toluene layer over anhydrous sodium sulfate, distilling off toluene and recrystallizing the resulting oily residue from ethyl alcohol to obtain 2-(3,4,5-trifluorophenyl)-5-pentyl-1,3-pyrimidine (7.8 g).

The following compounds were obtained in the same manner as above:
Compound No.
172. 2-(3,4,5-trifluorophenyl)-5-methyl-1,3-pyrimidine
173. 2-(3,4,5-trifluorophenyl)-5-ethyl-1,3-pyrimidine
174. 2-(3,4,5-trifluorophenyl)-5-propyl-1,3-pyrimidine
175. 2-(3,4,5-trifluorophenyl)-5-butyl-1,3-pyrimidine
176. 2-(3,4,5-trifluorophenyl)-5-hexyl-1,3-pyrimidine
177. 2-(3,4,5-trifluorophenyl)-5-heptyl-1,3-pyrimidine
178. 2-(3,4,5-trifluorophenyl)-5-octyl-1,3-pyrimidine
179. 2-(3,4,5-trifluorophenyl)-5-nonyl-1,3-pyrimidine
180. 2-(3,4,5-trifluorophenyl)-5-decyl-1,3-pyrimidine 181. 2-(3,4,5-trifluorobiphenyl-4'-yl)-5-methyl-1,3-pyrimidine
182. 2-(3,4,5-trifluorobiphenyl-4'-yl)-5-ethyl-1,3-pyrimidine
183. 2-(3,4,5-trifluorobiphenyl-4'-yl)-5-propyl-1,3-pyrimidine
184. 2-(3,4,5-trifluorobiphenyl-4'-yl)-5-butyl-1,3-pyrimidine
185. 2-(3,4,5-trifluorobiphenyl-4'-yl)-5-pentyl-1,3-pyrimidine
186. 2-(3,4,5-trifluorobiphenyl-4'-yl)-5-hexyl-1,3-pyrimidine
187. 2-(3,4,5-trifluorobiphenyl-4'-yl)-5-heptyl-1,3-pyrimidine
188. 2-(3,4,5-trifluorobiphenyl-4'-yl)-5-octyl-1,3-pyrimidine
189. 2-(3,4,5-trifluorobiphenyl-4'-yl)-5-nonyl-1,3-pyrimidine
190. 2-(3,4,5-trifluorobiphenyl-4'-yl)-5-decyl-1,3-pyrimidine Use example 1

A liquid crystal composition A consisting of

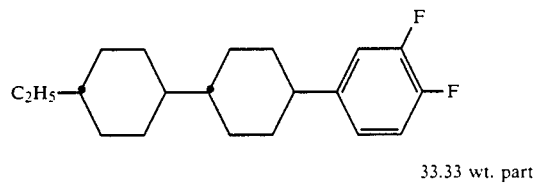

33.33 wt. part

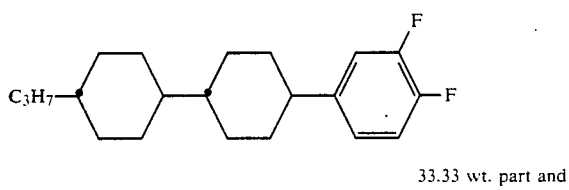

33.33 wt. part and

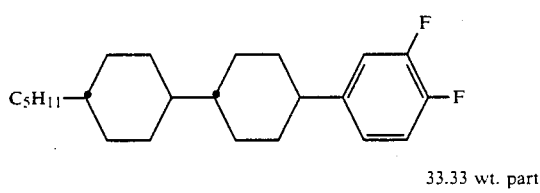

33.33 wt. part exhibited an N-I point of 112.4° C., a viscosity at 25° C. of 25.7 cP and a $\Delta n$ of 0.081. This liquid crystal composition was sealed in a TN cell of 8.7 μm thick and the threshold voltage was observed to exhibit 2.56 V. When 15 parts by weight of a compound (Compound No. 1 of Example 1 of the present invention) were added to 85 parts by weight of the above liquid crystal composition, the resulting liquid crystal composition exhibited an N-I point of 77.7° C. and a viscosity at 20° C. of 17.9 cP. This liquid crystal composition was sealed in the above TN cell and when its threshold voltage was observed, it lowered down to 1.94 V.

Use example 2

A liquid crystal composition consisting of 85 parts by weight of the liquid crystal composition A used in Use example 1 and 15 parts by weight of a compound (Compound No. 31) shown in Example 4 of the present invention was prepared. This liquid crystal composition exhibited an N-I point of 110.7° C. and a viscosity at 20° C. of 25.0 cP. When this liquid crystal composition was sealed in the above-mentioned TN cell, the resulting threshold voltage was 2.32 V.

Use example 3

A liquid crystal composition consisting of 85 parts by weight of the liquid crystal composition used in Use example 1 and 15 parts by weight of a compound shown in Example 6 (Compound No. 51) was prepared. This liquid crystal composition exhibited an N-I point of 107.4° C. and a viscosity at 20° C. of 24.9 cP. When this composition was sealed in the above TN cell, the resulting threshold voltage was 2.12 V.

Use example 4

A liquid crystal composition consisting of 85 parts by weight of the liquid crystal composition used in Use example 1 and 15 parts by weight of a compound of the present invention shown in Example 9 (Compound No. 81) was prepared. This liquid crystal composition exhibited an N-I point of 110.0° C. and a viscosity at 20° C. of 25.7 cP. When this liquid crystal composition was sealed in the above-mentioned TN cell, the resulting threshold voltage was 2.38 V.

The compound provided by the present invention has a large dielectric anisotropy value $\Delta \epsilon$ and a low viscosity; hence when the compound is used, it is possible to reduce the driving voltage of the resulting liquid crystal composition without raising its viscosity.

What we claim:

1. A trifluorobenzene derivative expressed by the formula

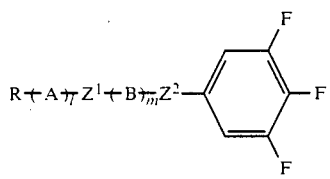

wherein R represents an alkyl group of 1 to 10 carbon atoms, —A— and —B— each represent 1,4-cyclohexylene or 1,4-phenylene, l represents 1 or 2, m represents 0, 1 or 2 and $1+m \leq 3$, and $Z^1$ and $Z^2$ each represent —CH$_2$CH$_2$— or a single bond, and when m is 0, $Z^2$ is a single bond.

2. A trifluorobenzene derivative according to claim 1, expressed by the formula

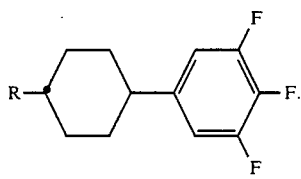

3. A trifluorobenzene derivative according to claim 1, expressed by the formula

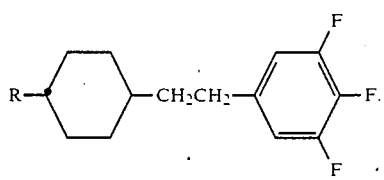

4. A trifluorobenzene derivative according to claim 1, expressed by the formula

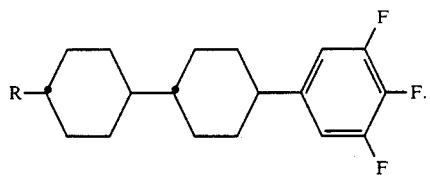

5. A trifluorobenzene derivative according to claim 1, expressed by the formula

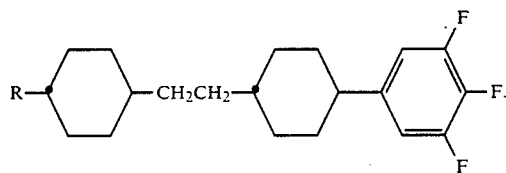

6. A trifluorobenzene derivative according to claim 1, expressed by the formula

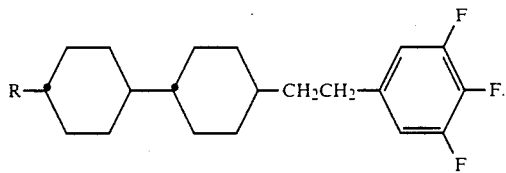

7. A trifluorobenzene derivative according to claim 1, expressed by the formula

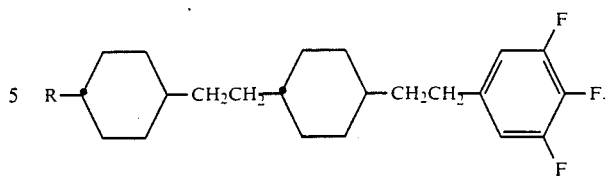

8. A trifluorobenzene derivative according to claim 1, expressed by the formula

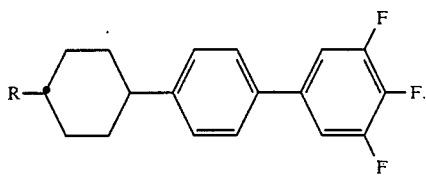

9. A trifluorobenzene derivative according to claim 1, expressed by the formula

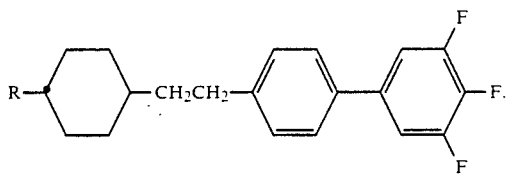

10. A liquid crystal composition comprising at least two components at least one of which is a trifluorobenzene derivative as set forth in claim 1, the content of which derivative is in the range of 2 to 40% by weight based on the weight of said composition.

* * * * *